US006455756B1

(12) United States Patent
Chen et al.

(10) Patent No.: US 6,455,756 B1
(45) Date of Patent: Sep. 24, 2002

(54) LONG TERM XENOGENEIC MYELOID AND LYMPHOID CELL PRODUCTION IN CHIMERIC IMMUNOCOMPROMISED MICE

(75) Inventors: Benjamin P. Chen, Fremont, CA (US); Christopher C. Fraser, Los Altos, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 08/290,038

(22) Filed: Aug. 12, 1994

(51) Int. Cl.$^7$ .................. A01K 67/00; A01K 67/033
(52) U.S. Cl. .................. 800/8; 800/9; 800/10; 800/11
(58) Field of Search .............. 800/2, 3, 8, 9, 800/10, 11; 424/9, 578

(56) References Cited

U.S. PATENT DOCUMENTS 5,411,749 A * 5/1995 Mayo et al. ............... 424/578

FOREIGN PATENT DOCUMENTS

EP 0 322 240 6/1989
WO WO 93/18144 9/1993

OTHER PUBLICATIONS

Namikawa et al. JEM 172: 1055, 1990.*
McCune et al. Ann. Rev. Immunol. 9:399, 1991.*
Mombaerts et al. Cell 68:869, 1992.*
Kyoizumi, et al. Blood 79:Apr. 4, 1992.*
H. Kaneshima, et al., Human Hematolymphoid Cells in Scid Mice, Immunology 1994, pp. 327–333.
Visser, et al., The Expression of Cytokine Receptors by Purified Hemopoietic Stem Cells, Stem Cells 1993; 11 (suppl2), pp. 49–55.
Mombaerts, et al., RAG–1–Deficient Mice Have No Mature B and T Lymphocytes, Cell, vol. 68, 869–877, Mar. 6, 1992.
Kyoizumi, et al., Implanation and Maintenance of Functional Human Bone Marrow in Scid–hu Mice, Blood, vol. 79, No. 7, Apr. 1, 1992, pp. 1704–1711.
McCune, et al., The Scid–hu Mouse: A Small Animal Model for HIV Infection and Pathogenesis, Annu. Rev. Immunol., 1991, pp. 399–429.
Namikawa, et al., Long–Term Human Hematopoiesis in the Scid–hu Mouse, J. Exp. Med., vol. 172, Oct. 1990, pp. 1055–1063.

Lapidot, et al., Cytokine Stimulation of Multilineage Hematopoiesis from Immature Human Cells Engrafted in Scid Mice, Science, vol. 255, pp. 1137–1141.
Kyoizumi, et al., Preclinical Analysis of Cytokine Therapy in the Scid–hu Mouse, Blood, vol. 81, No. 6, Mar. 15, 1993, pp. 1479–1488.
Nolta, et al., Sustained Human Hematopoiesis in Immunodeficient Mice by Cotransplantation fo Marrow Stroma Expressing Human Interleukin–e: Analysis of Gene Transduction of Long–Lived Progenitors, Blood, vol. 83, No. 10, May 15, 1994, pp. 3041–3051.
Vormoor, et al., Immature Human Cord Blood Progenitors Engraft and Proliferate to High Levels in Severe Combined Immunodeficient Mice, Blood, vol. 83, No. 9, May 1, 1994, pp. 2489–2497.
Nonoyama, et al., Strain–Dependent Leakiness of Mice with Severe Combined Immune Deficiency, Jour. of Immun., vol. 150, No. 9, May 1, 1993, pp. 3817–3824.
Gerling, et al., Multiple Low–Dose Streptozocin–Induced Diabetes in NOD–scid/scid Mice in the Absence of Functional Lymphocytes, Diabetes, vol. 43, Mar. 1994, pp. 433–440.
Bosma, et al., A Severe Combined Immunodeficiency Mutation in the Mouse, Nature, vol. 301, 1983, pp. 527.
Johnson et al., "Feline Lymphoid Tissues Engrafted into Scid Mice Maintain Morphologic Structure and Produce Feline Immunoglobulin", *Lab Anim Sci* (Aug. 1994) 44(4):313–318.
Peault et al., "Identification of a Novel Rare, Human Bone Marrow Population with Hematopoietic Stem Cell Activity II In Vivo Studies in Immunodeficient Scid Mice Engrafted with Human Blood–Forming Organs", Experimental Hematology (1991), 19(6):468.

* cited by examiner

*Primary Examiner*—Anne-Marie Baker
(74) *Attorney, Agent, or Firm*—J. Timothy Maigs; Douglas A. Golightly

(57) ABSTRACT

Immunocompromised mammalian hosts are subcutaneously implanted with a combination of human fetal bone and spleen. The chimeric animals can produce human B-cells, myeloid cells and T-cells for up to 9 months in vivo when supplied with an allogeneic human fetal thymic fragment at the same site. Grafts contain cell populations expressing CD4 and CD8, CD19 or CD33, CD14 and CD15, all of which also express the HLA type of the fetal bone/spleen. T-cells derived from progenitors in the fetal bone/spleen contain both mature single positive CD4+CD8−, CD8+CD4− as well as a high percentage of immature double positive CD4+CD8+ populations.

14 Claims, No Drawings

LONG TERM XENOGENEIC MYELOID AND LYMPHOID CELL PRODUCTION IN CHIMERIC IMMUNOCOMPROMISED MICE

TECHNICAL FIELD

The field of this invention is immunocompromised mammals comprising xenogeneic tissues which are capable of long term reconstitution of myeloid and lymphoid cells.

BACKGROUND

Hematopoiesis is a continuous process of differentiation and amplification, replacing billions of mature lymphoid and myeloid cells in the normal human every day. This process depends on the continuous turnover of hematopoietic stem cells, which have the capacity for self-maintenance, extensive proliferation, and multipotentiality. These characteristics have been studied in great detail in the murine system, particularly through the uses of sequential bone marrow transplants and genetic marking using chromosomal rearrangements or retroviruses. Similar studies with human hematopoietic stem cells have lagged, primarily due to a lack of an equivalent model for long-term multipotential differentiation.

Scientists have recently succeeded in demonstrating human hematopoietic progenitor engraftment and differentiation in immunodeficient mice. Of particular interest has been the use of such mice for studying the tissue, its response to drugs and changes in the environment of the tissue. Various aspects of the human tissue may be studied in an environment simulating the natural environment using such chimeric animals.

Significant advances have been made in understanding the earliest events in human hematopoietic development by transplanting human cells or tissues into immunocompromised mice and observing human hematopoiesis for prolonged periods. However, each of the prior art systems is limited in its ability to study concomitant human mature T-cell, mature B-cell and myeloid cell production from a common stem cell pool. Implants of human fetal thymus and liver are limited in the extent to which myeloid and B-cells will develop. It is therefore of interest to develop a chimeric animal which is capable of long term reconstitution of myeloid, as well as both B- and T-lineages of the hematopoietic system.

Relevant Literature

A description of the SCID-hu mouse may be found in J. M. McCune et al. (1988) *Science* 241:1632–1639; R. Namikawa et al. (1990) *J. Exp. Med.* 172:1055–1063 and J. M. McCune et al. (1991) *Ann. Rev. Immunol.* 9:395–429. Implantation of functional bone marrow is described in S. Kyoizumi et al. (1992) *Blood* 79:1704. European patent application no. 469 632 discloses the use of immunocompromised mammals with a thy-liv implant.

Cytokine stimulation of multilineage hematopoiesis from immature human cells engrafted in SCID mice is described in T. Lapidot et al. (1992) *Science* 255:1137; J. Nolta et al. (1994) *Blood* 83:3041; and S. Kyoizumi et al (1993) *Blood* 81:1479–1488. The proliferation and engraftment of immature cord blood progenitors in such mice is further discussed in J. Vormeer et al. (1994) *Blood* 83:2489.

Immunocompromised mouse strains are described in S. Nonoyama et al. (1993) *J. Immunol* 150:3817–3824; I. Gerling et al. (1994) Diabetes 43:433–440; Bosma, et al. (1983) *Nature* 301:52; and P. Mombaerts et al. (1992) *Cell* 68:869–877.

SUMMARY OF THE INVENTION

Immunocompromised hosts are provided, comprising xenogeneic functioning hematolymphoid tissue comprising bone marrown spleen and optionally, thymus tissue. The tissue grows to form a hybrid organ structure capable of producing B-lineage lymphocytes, T-lineage lymphocytes and myeloid cells.

DESCRIPTION OF THE SPECIFIC EMBODIMENTS

Methods and compositions are provided for the production of human hematopoietic cells with a plurality of lineages in an immunocompromised heterologous mammalian host, particularly a mouse, for extended periods of time. The method comprises combining non-dispersed bone and spleen fragments in juxtaposition, optionally together with a thymus fragment, in an appropriate site in an immunocompromised host. The chimeric animal is useful for studying human hematopoiesis and pathogenesis in an experimental setting.

The co-implantation of human bone and spleen tissue is sufficient to support the growth of hematopoetic progenitors which, in the absence of a thymus implant, are able to mature into myeloid lineage cells as evidenced by expression of CD33, including granulocytes, as evidenced by the expression of CD14 and CD15; monocytes; and B lineage cells, as evidenced by the expression of CD19 and CD20. Myeloid cells may include neutrophils, monocytes and macrophages, eosinophils, basophils and mast cells, and progenitors thereof. Some T cell subsets are also present in the bone and spleen implant, as shown by the expression of CD4. However, maturation of T cell progenitors to provide all T cell subsets, particularly those that express CD8, requires the presence of a co-implantation of thymus, which provides stromal and epithelial cells necessary for differentiation. When thymus tissue is present, a subset of progenitor cells derived from the bone/spleen co-implant are able to differentiate into T cells, including $CD4^+CD8^+$, $CD4^+CD8^-$ and $CD4^-CD8^+$ subsets.

The host animal is engrafted with both spleen and bone, where the tissue implants are normally contiguous to provide a continuous source of hematopoietic progenitor cells. The spleen tissue appears to amplify to partially or wholly surround the growing human fetal bone and thymus to form a hybrid tissue, which provides a continuous source of myeloid cells, B-cells and other lymphoid progenitor cells. To provide for maturation of T cells, human thymus is also engrafted, in close proximity, usually in contact with the bone and spleen tissue. The thymus tissue may have a different HLA allotype from the spleen and bone. Differences in HLA have shown that mature T-cells are derived from stem cells present in the spleen/bone graft. Such animals are useful in determining the contribution that thymic stromal and epithelial elements, or hematopoietic progenitor cells make to T-cell maturation. The hybrid organ, containing bone, thymus and spleen (BTS), is vascularized, and able to survive in the host for long periods of time. The hybrid tissue may be used after at least about 3 weeks, more usually after at least about 6 weeks, and the hybrid tissue will remain functional for at least about 9 months, or more.

A suitable site for implantation must be able to accomodate the size of the implanted tissue and to keep the implanted tissues in close proximity. Of particular interest is subcutaneous implantation. The position of the subcutaneous implant on the body of the host is not critical, but the area of the mammary fat pads may conveniently be used. The tissue will be implanted, conveniently by incision of the host skin and placement with a trocar, etc.

The BTS tissue transplant may be only one of other tissues transplanted into the host. For example, in addition to the BTS implant, other hematopoietic components may be included, such as stem cells, lymph nodes, embryonic yolk sac, fetal liver, pancreatic tissue, appendix tissue, tonsil tissue and the like, which may serve in the development of a hematopoietic system in the immunocompromised host for a variety of purposes. Sites for introduction of additional tissue may include under the spleen capsule, abdominal wall muscle, under the renal capsule, in the eye, the peritoneum, the peritoneal lining, brain, subcutaneous, vascular system, spinal cord, membranous sacs or capsules of various tissue, the retroperitoneal space, reproductive organs, etc.

Introduction of the secondary tissue may be achieved by injection, implantation, or joining blood vessels (and other vessels if necessary) of the donor and host, using intravenous catheters, trocars, and/or surgical incision, or the like. The tissue or cells of interest will generally be normal, e.g. non-transformed and non-malignant tissue or cells. With various organs one may include native surrounding tissue with the organ tissue itself. The surrounding tissue may comprise connective tissue, or portions of blood and lymphatic vessels. In some cases, whole organ grafts may be transplanted by anastomosing donor and host blood vessels, lymphatic vessels, and the like. For the most part, normal cells, tissue, and/or organs may be stably maintained and functional for at least about 3–6 months and frequently for at least about 10 months.

As appropriate, dispersed cells may be employed, where the relevant organs are teased apart to yield viable cells in suspension. Cells of particular interest as a secondary implant are human hematopoietic cells, particular committed progenitor cells and stem cells. The progenitor cells may be mismatched as to HLA type with the hybrid tissue, so as to provide a marker for differentiating cells. The progenitor cells may be injected into the bone marrow cavity before or after implantation, and the resulting repertoire of lineages analyzed. Ablation of endogenous hematopoietic cells in the bone, e.g. radiation, may be desirable to improve the frequency of engrafted cells. Multilineage stem cell assays can be performed in this manner. The repertoire of lineages which are able to develop from a particular progenitor cell type, and the effects of various treatments of those cells, e.g. exposure to growth factors, cytokines, mutagens, etc. is determined.

A mixed population of cells in suspension may be enriched for the particular cells of interest. For example, with bone marrow cells, the suspension may be enriched for hematopoietic precursors by Ficoll-hypaque density gradient centrifugation, fluorescence activated cell sorting, panning, magnetic bead separation, elutriation within a centrifugal field, or rosetting.

In some instances it may be desirable to enrich cells by killing or removing other cells. This may be achieved by employing monoclonal antibodies specific for the undesired cells in the presence of complement or linked to a cytotoxic agent, such as a toxin, e.g. ricin, abrin, diphtheria toxin, or a radiolabel, e.g. $^{131}$I, or the like. Immunoaffinity columns may be employed which allow for specific separation of either the desired or undesired cells, depending on the nature of the mixture.

The human fetal tissue, either BTS or an additional implant, may be fresh tissue, obtained within about 48 hours of death, or freshly frozen tissue, tissue frozen within about 12 hours of death and maintained at below about −10° C., usually at about liquid nitrogen temperature (−70° C.) indefinitely. The tissue may be from an organ implanted in a chimeric host, where the tissue may be removed from 2–4 weeks after implantation, or longer. In this manner, the tissue originally obtained from the host source may be greatly expanded, substantially increasing the total number of chimeric hosts which may be obtained. The tissue obtained from the chimeric host may be treated analogously to the tissue obtained from the human source. Normally the tissue will not have been subject to culture in vitro for an extended period of time.

The thymus and spleen tissue are provided as pieces of whole organs, and will include such stromal and epithelial cells as are normally present. The size of implanted tissue will generally be from about 0.5 to 4 mm, more usually from about 1 to 2 mm, so that the sections can easily fit into a trocar used for implantation, usually conveniently of about 15- to 20-gauge. The bone marrow may be fetal or adult, preferably fetal. Long bones are employed, such as tibia, femur, humerus or the like. The bone will generally be at least about 0.5 cm in length and may be 2 cm in length or greater, depending upon the size of the host. For a mouse host, 1 cm is found to be a convenient size. The bone may be cut along a longitudinal axis, so that the bone cortex as well as intramedullary regions are exposed to allow for vascularization, or cross-sectional to provide tubular slices.

For the most part the donor tissue will be human, although cells from sources other than members of the same family as the host animal may find use. The source of the tissue will usually be fetal. Preferably the tissue will be from a child of less than about 3 years, preferably less than about 1 year and at or younger than neonate, more preferably being fetal tissue of from about 7 to 24 weeks. In some cases adult human bone may be implanted, as tubular slices or chips.

For different organs differently aged tissue may be preferred. For fetal tissue, it is desirable that the human lymph be equal to or greater than about 20 gestational weeks (g.w.), preferably 20–24 g.w.; and for human thymus and liver, from about 16–24 g.w., preferably greater than 18 g.w. For fetal bones and spleen, the fetus will generally be from about 16 to 24 g.w.

Immunocompromised mammalian hosts suitable for implantation and having the desired immune incapacity exist or can be created. The significant factor is that the immunocompromised host is incapable naturally, or in conjunction with the introduced organs, of mounting an immune response against the xenogeneic tissue or cells. Therefore it is not sufficient that a host be immunocompromised, but that the host may not be able to mount an immune response after grafting, as evidenced by the inability to produce functional syngeneic host B-cells, particularly plasma cells, and/or T-cells, particularly CD4$^+$ and/or CD8$^+$ T-cells after implantation. Of particular interest are small mammals, e.g. rabbits, gerbils, hamsters, guinea pigs, etc., particularly murines, e.g. mouse and rat, which are immunocompromised due to a genetic defect which results in an inability to undergo germline DNA rearrangement at the loci encoding immunoglobulins and T-cell antigen receptors.

Presently available hosts include mice that have been genetically engineered by transgenic disruption to lack the recombinase function associated with RAG-1and/or RAG-2 (e.g. commercially available TIM™ RAG-2 transgenic), to lack Class I and/or Class II MHC antigens (e.g. the commercially available C1D and C2D transgenic strains), or to lack expression of the Bcl-2 proto-oncogene. Of particular interest are mice that have a homozygous mutation at the scid locus, causing a severe combined immunodeficiency which is manifested by a lack of functionally recombined immunoglobulin and T-cell receptor genes. The scid/scid mutation is available or may be bred into a number of different genetic backgrounds, e.g. CB. 17, ICR (outbred), C3H, BALB/c, C57B1/6, AKR, BA, B10, 129, etc. Other mice which are useful as recipients are NOD scid/scid; SGB scid/scid, bh/bh; CB.17 scid/hr; NIH-3 bg/nu/xid and META nu/nu. Transgenic mice, rats and pigs are available which lack functional T cells due to a homozygous disruption in the CD3ε gene. Immunocompromised rats include HsdHan:RNU-rnu; HsdHan:RNU-rnu/+; HsdHan:NZNU-rnu; HsdHan:NZNU-rnu/+; LEW/HanHsd-rnu; LEW/HanHsd-rnu/+; WAG/HanHsd-rnu and WAG/HanHsd-rnu/+. The availability of scid/scid mice with an NOD (non-obese diabetic) background provides an opportunity to study the effect of human T cells in the development of insulin dependent diabetes.

Additional loss of immune function in the host animal may be achieved by decreasing the number of endogenous macrophages before, during, or after implantation of the xenogeneic tissue. Of particular interest is the reduction of macrophages by administration of dichloromethylene diphosphonate ($Cl_2MDP$) encapsulated in liposomes, as described in co-pending application Ser. No. 08/169,293. Elimination of host macrophages improves the ability of non-autologous hematopoietic cells to survive in the host animal's circulation.

The host will usually be of an age less than about 25% of the normal lifetime of an immunocompetent host, usually about 1 to 20% of the normal lifetime. Generally, the host will be at least about six weeks old and large enough to manipulate for introduction of the donor tissue at the desired site. For example, mice are usually used at about 6 to 10 weeks of age. Growth of the tissue within the host will vary with the organ.

The mammalian host will be grown in conventional ways. Depending on the degree of immunocompromised status of the mammalian host, it may be protected to varying degrees from infection. An aseptic environment is indicated. Prophylactic antibiosis for protection from Pneumocystis infection may be achieved for scid/scid mice with 25–75 mg trimethoprim and 100–300 mg sulfamethoxazole in 5 ml of suspension, given three days each week, or in impregnated food pellets. Alternatively, it may be satisfactory to isolate the potential hosts from other animals in gnotobiotic environments after cesarean derivation. The feeding and maintenance of the chimeric host will for the most part follow gnotobiotic techniques.

The presence of the foreign tissue in. an immunocompromised host may be used to study the effect of various compounds on the growth, viability, differentiation, maturation, transformation, or the like, of the human cells in a live host. The chimeric host may be used to study the effect of a variation of a condition on a symptom or indication of a disease. By condition, it is intended a physical, chemical or biological property, e.g. temperature, electric potential, ionic strength, drugs, transformation, etc.

It is of particular interest to study the pathogenesis of various infectious agents and/or the effect of various drugs or treatments on the induction or progress of disease. Infectious agents of interest include bacteria, such as Pneumococcus, Staphylococcus, Streptococcus, Meningococcus, Gonococcus, Eschericia, Klebsiella, Proteus, Pseudomonas, Salmonella, Shigella, Hemophilus, Yersinia, Listeria, Corynebacterium, Vibrio, Clostridia, Chlamydia, Mycobacterium, Helicobacter and Treponema; protozoan pathogens, and viruses. Viruses of interest include human immunodeficiency viruses (HIV-1 and HIV-2); enteric viruses, e.g. coxsackie, echovirus, reovirus; respiratory viruses, e.g. rhinovirus, adenovirus, coronavirus, parainfluenzavirus, influenzavirus; picornavirus; rhabdovirus; rubeola; poxvirus; herpesvirus; EBV; paramyxovirus (measles), hepatitis viruses A, B, C and D, varicella zoster virus (chicken pox) and cytomegalovirus.

Of particular interest are human tropic viruses, which infect or cause disease in human cells, many of which cannot easily be studied in conventional animal models. In general, human tropic viruses primarily cause productive infections, i.e. infection which results in viral replication and release of new infectious particles, in human cells. The virus may infect cells of closely related primate species, but will usually not cause the disease symptoms seen in humans, e.g. measles virus. The reason for such a tropism to human cells may be due to specific binding of the virus to a particular cell surface antigen required for entry of the virus into the cell. Examples of this specificity are the binding of HWV-1 to human CD4, the binding of herpes simplex-1 to human fibroblast growth factor receptor, and of measles virus to human CD46. Other viruses may require cytoplasmic components of human cells in order to complete a cycle of replication. Human tropic viruses include HIV-1 and HIV-2; the human herpesviruses: HSV-1, HSV-2, varicella zoster virus, Epstein-Barr virus, human B-cell lymphotropic virus and human cytomegalovirus; smallpox virus; measles virus and hepatitis B virus.

The virus may be wild-type, e.g. clinical isolates, conventional strains, etc.; attenuated strains; or may be genetically engineered to enhance or reduce infectivity, pathogenicity, etc. Such modifications in the viral genome may include deletion of virulence genes, mutations in viral coat proteins which alter the host range, change in viral nucleic acid polymerases, alterations in proteins which affect integratation of the viral genome into the host genome, etc. Mutations introduced into the viral genome are useful to map the functions of viral proteins, and to determine which domains are responsible for various aspects of the infection, i.e. in establishing latency, transforming cells, viral replication, etc.

To study the effects of of infection on human cells, a "BTS" implant is inoculated with an infectious level of virus. The effect of the virus is determined, usually as a function of time. Data may be obtained as to the immune response of human cells to the virus; products which are secreted by infected or involved cells in response to infection, e.g. cytokines, interferons, antibodies, etc.; the viability and growth of the human lymphocytes, myeloid cells, and stromal cells which are present either in the "BTS" implant or in the host circulation; and virus replication, e.g. release of new infectious particles.

Infection may be achieved by direct injection of the virus. Usually, the injection will involve at least about $10^2$ infectious units, preferably from about $10^3$ to $10^5$ infectious units of virus. The virus may be a clinical isolate, a cloned clinical isolate, a genetically modified isolate, or the like. Alternatively, viruses may be administered by injection of infected cells, where the injected cells will produce infectious virus over time. The cells will deliver a dose of virus of at least about $10^2$ infectious units, preferably from about $10^3$ to $10^5$ infectious units of virus.

Various drugs may be administered to the host and the effect on a particular tissue determined by invasive or non-invasive techniques. Non-invasive techniques include NMR, CAT scans, fluoroscopy, roentgenography, radionuclide scanning, ultrasonography, electrocardiography, electroencephalography, evoked potentials, etc. Invasive techniques include biopsy, autopsy, laparotomy, intermittent intravenous blood sampling, or intravenous catheterization, etc. Convenient placement of various devices, e.g. catheters, electrodes, etc. may be performed for continuous monitoring. Thus, the host may be used to determine the carcinogenicity of various compounds to different human tissues, the effect on growth and viability of various human tissues, the effect of combinations of compounds, e.g. drugs, or the like. In addition, by providing for pathogenic infection of the xenogeneic tissue, the effect of various drugs in protecting the host tissue from the pathogen, as well as being cytotoxic to or suppressive of the pathogen in a cellular environment can be determined.

The chimeric hostmay also be used for evaluating the cytotoxicity of various drugs toward human tissue, for example, for screening for investigative new drug applications. In addition, the chimeric hosts may be used for evaluating drugs as to their efficacy, safety and bioavailability. Use of the chimeric animal in studying the effect of drugs on infection may begin with administration of-the drug prior to, substantially concomitant with, or subsequent to the administration of the infectious dose of virus. Administration of the drug will usually begin not earlier than 7 days prior to infection, more usually not more than about 1 day prior to infection. In most cases, administration of the drug will begin not later than about 7 days after infection, more usually not later than about 1 day after infection. However, for studies of chronic infections, drug treatment may be started after as much as. one year after infection, usually after six months, more usually after one month. After initial screening, different periods of time may be of interest in establishing the effectiveness of the drug.

The manner of administration will vary greatly, depending upon the nature of the drug. It may be provided orally, ad libitum, intraperitoneally, intravascularly, subcutaneously, intrathymically, or the like. Usually, different dosage levels will be employed, based on past experience with the drug, anticipated levels with human treatment, toxicity or side effects, experience with the particular chimeric host, and the like. The effect of the drug may be monitored for any convenient time, usually at least 1 week from the initiation of administration of the drug, more usually at least 2 weeks, and at times for periods as long as 6 weeks or more. Preferably, determinations will be made in the period from about 2–6 weeks.

For the effectiveness of drugs in suppressing HIV-induced T-cell or thymocyte depletion, various measurements can be made. By employing flow cytometry (fluorescence-activated cell scanning flow cytometry), one can analyze the CD4 and CD8 profile of the peripheral blood, the cell population in a cell dispersion prepared from the thymus, lymph node implant, or other human fetal tissue which is present, as appropriate. One may also monitor for the presence of HIV, by monitoring the level of p24 in the peripheral blood or the implant, HIV RNA or portion thereof, or HIV DNA, using the polymerase chain reaction. In addition, one may use histological analysis, employing immunochemistry, for detecting the presence of CD4 or CD8, proteins of HIV, e.g. p24, which are present in the implant. One may also analyze for indications of apoptosis in the infected tissue, as indicated by multiple foci of cells with condensed nuclear material as seen by histologic methods or election microscopy or as determined by methods which can discern a DNA degradation profile consistent with apoptosis.

Phenotyping of the xenogeneic cells to verify their origin and stage of developmental progression may be performed by standard histological methods, by immunohistochemistry, antibody staining or in situ hybridization with RNA and/or DNA probes. The exact method is not critical to the invention, and will depend on the exact cell types being studied. HLA markers may be used to distinguish the established xenogeneic organ transplants. The HLA type can be readily determined by staining with an appropriate antibody directed against any of the alleles of the human HLA locus, including Class I and Class II antigens.

The presence of mature human T-cells, B-cells and myeloid cells in an animal model allows the development of human antibodies to a specific antigen. The human cells are able to interact so as to provide T-independent and T-dependent antibody responses, e.g. class-switching from IgM to IgG and IgA subclasses, and affinity maturation of antibody binding. The desired antigen will generally be formulated with an adjuvant. The animals are immunized systemically, e.g. i.v., or intra-muscularly, or intragraft. The animals are boosted with antigen as necessary. A bleed is done on the immunized animals to test the titer of serum antibodies against the immunizing antigen. If production of hybridoma antibodies is desired, the graft will then be removed, and a cell suspension made. The BTS cells are then fused to a myeloma cell partner. The resulting hybridoma cells are screened for reactivity against the immunizing antigen, and positive cells selected for antibody production.

The following examples are offered by way of illustration and not by way of limitation.

Experimental

Example 1

Construction and Analysis of the BTS Implant
Materials and Methods

BTS mice. CB.17 scid/scid mice were obtained from the Jackson Laboratory, Bar Harbor, Me. The mice were housed in standard isolator cages within a routine animal holding facility. To prevent infections, an antiobiotic prophylaxis of trimethoprin/sulfamethoxasole (40 mg/200 mg per 5 ml of suspension; 0.125 ml of suspension per 4 ml of drinking water per mouse per day) was administered. BTS mice were constructed using small (2 mm) human fetal spleen and thymus fragments and approximately 5×3×10 mm fetal bone fragments from femurs and tibias of 19 to 23 week gestational fetuses from elective abortuses. Fetal tissues were obtained with informed consent from agencies according to federal and state regulations. The tissue was obtained directly in the operating room as fetal parts. Without maintaining strict sterility the parts were taken immediately to a gross dissection room. The identified tissue was dissected out and placed into RPMI 1640 medium with 10% fetal calf serum. Fetal spleen and thymus fragments were placed adjacent to a fetal bone fragment subcutaneously in the mammary fat pad of 6 to 8 week old anesthetized C.B-17 scid/scid mice. The recipient mice were removed from the microisolator and placed in a vertical laminar air-flow hood, anesthetized with ketamine and taped on sterile operating boards. By an aseptic technique, the fourth mammary fat pads were exposed through a midline ventral incision. Sharpened watchmakers forceps were used to create a defect in the mammary fat pad through which the fetal tissue was introduced. The ventral skin incision was then closed with 7.5 mm wound clips. Cell suspensions from fetal thymus or fetal liver were used to determine HLA types for individual donors.

Antibodies. Mouse antibodies against human leukocyte markers were directly conjugated with phycoerythrin (PE), fluorescein isothiocyanate (FITC) or tri-color (TC). These included antibodies against human CD14, CD15, CD33 and CD8 (Becton Dickinson, Mountain View, Calif.) and CD4, CD19, and CD45 (Caltag, South San Francisco, Calif.). HLA immunophenotype was determined using FITC-conjugated anti-human HLA class I MAb MA2.1, BB7.1, BB7.2, MB40.2 and GAP-A3, derived from hybridomas obtained from ATCC (Rockville Md.) and fluorochrome conjugated at SyStemix. Irrelevant isotype controls were directly FITC or PE conjugated IgG1 (Becton Dickinson, Mountain View, Calif.) and TC-conjugated IgG2A (Caltag, South San Francisco, Calif.).

Flow Cytometry. BTS mice were sacrificed 28–36 weeks post transplant and human tissue grafts removed. Single cell suspensions were made by scraping and mincing the grafts in cold phosphate buffered saline containing 0.2% BSA. The cells were washed and blocked with 1 mg/ml human gamma-globulin (Gamimune, Miles Inc., Elkhart, Ind.). Total viable cell content was determined by trypan blue dye exclusion, and cells incubated for 30 minutes on ice with directly conjugated antibodies. Cells were washed and analyzed on a FACScan fluorescent analyzer (Becton Dickinson).

Results

A Common Progenitor Cell Pool Contributes to Long Term Multilineage Human Hematopoiesis in BTS Mice. CB.17 scid/scid mice were implanted subcutaneously with fetal bone and spleen, and an HLA-mismatched thymus fragment, sacrificed 28–36 weeks later and the grafts analyzed by FACS for human hematopoietic cells derived from the fetal bone-spleen. A total of 32 grafts were analyzed, of those 22 (68.8%) were found to have greater than 5% human cells.

Cell suspensions were stained with combinations of anti-donor Class I (specific to the bone-spleen fragments and not the thymus fragment), CD4 and CD8, or anti-donor Class I, CD33 and CD19. A high proportion of CD4 and CD8 positive T-cells stain for anti-HLA specific to cells derived from the bone and spleen graft (donor). In addition in the same grafts donor derived CD19 positive cells (B-cells) and CD33 positive (myeloid cells) are also easily detectable. The data from 22 grafts from 4 different bone-spleen, thymus sets (A/B, C/D, E/F, and G/H) are shown in Table 1.

Proportions of donor-derived CD4 and CD8 positive T-cells as well as of C19 and CD33 positive cells were determined by the number of cells positive for donor class I above the isotype control. Of 24 grafts shown in Table 1, 15 (62.5%) had multilineage hematopoiesis with detectable levels of T, B and myeloid cells as determined by FACS phenotyping. The remainder of the grafts had different bi-lineage or single lineage donor derived cells, with 2 grafts having detectable levels of B and myeloid cells, 2 grafts with donor T-cells only, 1 graft with T-cells and B-cells and 1 graft with T-cells and myeloid cells.

It has been previously shown that fetal bone fragments can maintain B-cell production and myelo-erythroid production, as well as maintain CD34+ cells in the graft for prolonged periods (European Patent application no. 91 911 224.3). However, by 20 weeks after implantation, hematopoiesis is significantly reduced in animals with bone implants alone. For periods of time significantly longer than 20 weeks, the subject bone/spleen and BTS mice show active hematopoiesis. The data shown in Table 1 indicate that early progenitors in the bone or spleen also have the capacity to reconstitute a fetal thymic fragment allowing T-cell production concurrent with myeloid and B-cell production in the same graft for periods of at least 36 weeks.

TABLE 1

Distribution of human hematopoietic cell types in SCID-hu BTS mouse grafts

| graft number | weeks post engraftment | engrafted tissue set | % CD4+ cells with bone/spleen HLA | % CD8+ cells with bone/spleen HLA | % CD19+ cells with bone/spleen HLA | % CD33+ cells with bone/spleen HLA |
|---|---|---|---|---|---|---|
| 1 | 28 | A/B | 16.5 | 14.8 | 0.6 | NDT |
| 2 | 28 | A/B | 44.5 | 38.2 | 9.9 | 1.4 |
| 3 | 28 | A/B | 6.3 | 4.8 | NDT | 0.5 |
| 4 | 28 | A/B | 10.3 | 6.6 | 13.5 | 1.9 |
| 5 | 28 | A/B | 3.3 | 0.6 | 25.6 | 2.3 |
| 6 | 28 | A/B | 31.1 | 24.3 | 13.8 | 1.5 |
| 7 | 32 | C/D | 1.1 | NDT | 42.8 | 0.9 |
| 8 | 32 | C/D | 3.0 | NDT | 46.4 | 2.7 |
| 9 | 32 | C/D | 1.1 | NDT | 33.0 | 0.9 |
| 10 | 32 | C/D | 1.9 | 1.1 | 46.2 | 1.7 |
| 11 | 32 | E/F | 47.1 | 50.2 | NDT | NDT |
| 12 | 32 | E/F | 36.3 | 36.3 | 1.8 | 0.8 |
| 13 | 32 | E/F | 9.2 | 5.7 | 33.6 | 2.0 |
| 14 | 36 | G/H | 32.2 | 33.8 | NDT | NDT |
| 15 | 36 | G/H | 27.5* | 30.9* | 23.9* | 19.8* |
| 16 | 36 | G/H | 11.4* | 14.8 | 17.2* | 9.8 |
| 17 | 36 | G/H | 75.6* | 76.6* | NDM | NDM |
| 18 | 36 | G/H | NDT | NDT | 43.1* | 3.9* |
| 19 | 36 | G/H | NDT | NDT | 46.3* | 5.9* |
| 20 | 36 | G/H | 4.7 | NDT | 81.7 | 3.8 |

TABLE 1-continued

Distribution of human hematopoietic cell types in SCID-hu BTS mouse grafts

| graft number | weeks post engraftment | engrafted tissue set | % CD4+ cells with bone/spleen HLA | % CD8+ cells with bone/spleen HLA | % CD19+ cells with bone/spleen HLA | % CD33+ cells with bone/spleen HLA |
|---|---|---|---|---|---|---|
| 21 | 36 | G/H | 3.4 | NDT | 80.6 | 2.7 |
| 22 | 36 | G/H | 11.3 | 0.8 | 30.4 | 6.9 |

SCID mice implanted with fetal bone, spleen (A, C, E, G) and HLA mismatched thymus (B, D, F, H) subcutaneously were sacrificed 28 to 36 weeks post transplant (weeks post), grafts removed and single cell suspensions made. Cells stained with MA2.1 = FITC (tissue A, C, E) or GAPA-3-FITC (tissue G) plus either CD8-PE and CD4-TC or CD33-PE and CD19-TC. The percentage of cells positive for donor HLA was determined by analysis on a FACscan. Percentages of less than 0.5% were considered not detectable (NDT). In 2 instances data from FACS plots was undeterminable (NDM). *Not corrected for isotype staining which is typically <0.5%.

Maintenance of Myeloid Cells in BTS Grafts. CD33 is expressed on immature myelocytic cells and monocytes. Recently, however, it has been shown that CD33 is also expressed on activated normal human peripheral blood CD4+ and CD8+ T-cells. In order to ensure that the CD33 staining reflected myeloid lineage differentiation, cell suspensions from each graft were stained with a combination of CD45, plus monocyte/granulocyte marker CD14 and granulocyte marker CD15. A large proportion of cells have low forward and side scatter properties when the total ungated populations of cells from this graft are analyzed, suggesting a substantial number of lymphoid cells are present, which was confirmed by staining for B-cell and T-cell lineage markers. Forward and side scatter properties of cells gated on donor Class I and CD33+ shows that most of these cells are not within the lymphoblastoid region. CD45+ cells stained with CD14 and CD15 demonstrate distinct populations of CD14/CD15 double positive cells as well as CD15 single positive granulocytes. These staining profiles plus the scatter properties of CD33 positive cells indicate that a fetal bone/spleen derived myeloid population exists in the BTS grafts for prolonged times.

BTS Grafts Contain Immature CD4+/CD8+ Double Positive as well as Mature Single Positive Donor Derived CD4+ and CD8+ T-cells. To determine the maturational stage of donor derived T-cells in the BTS grafts, three color staining of grafts with donor Class I plus CD4 and CD8 was performed. If early T-cell or multilineage progenitors within the fetal bone/spleen are capable of sustained long-term contribution to T-cell production in the thymic microenvironment, similar to that found in normal fetal thymus or in Thy/Liv grafts, immature CD4+CD8+ double positive (DP) as well as mature single CD4+ or CD8+ positive cells (SP) should be observed. Of the 22 grafts analyzed for phenotype, 15 (68.2%) had detectable levels of both CD4+ and CD8+ single positive mature T-cells. Immature DP T-cells were observed in 12 of 22 grafts (55%). Values for the proportion of CD4+ and CD8+ SP cells compared to CD4+CD8+ DP cells were normalized to the total T-cell production based on CD4 and CD8 expression and are shown in Table 2. The proportion of total DP T-cells ranged from 17.6% to 82.6% in the total T-cell population. This analysis excludes early CD4 and CD8 negative T-cell precursors, but indicates a high proportion of grafts contain substantial number of intermediate DP cells and that active T-cell development is continuing.

TABLE 2

Distribution of CD4 and CD8 in BTS mouse graft T-cells

| graft number | CD4 | CD8 | CD4/CD8 |
|---|---|---|---|
| 1 | 12.4 | 4.9 | 82.6 |
| 2 | 21.1 | 10.8 | 68.1 |
| 3 | 34.5 | 7.7 | 57.5 |
| 4 | 34.0 | 9.8 | 56.3 |
| 5 | 74.0 | 8.1 | 17.6 |
| 6 | 25.7 | 13.4 | 60.9 |
| 10 | 66.7 | 33.3 | NDT |
| 11 | 10.4 | 10.7 | 78.9 |
| 12 | 24.5 | 20.7 | 54.8 |
| 13 | 41.7 | 10.4 | 47.8 |
| 14 | 18.2 | 10.2 | 71.5 |
| 15 | 43.1 | 36.8 | 20.2 |
| 16 | 42.9 | 57.1 | NDT |
| 17 | 10.8 | 7.6 | 81.6 |
| 22 | 59.0 | 41.0 | NDT |

Grafts from SCID mice implanted with fetal bone, spleen and HLA mismatched thymus were analyzed. Graft numbers are the same as those given in Table 1. Analysis of the frequency of total single CD4 positive, single CD8 positive and double CD4/CD8 positive cells are shown. Values are percentages of the total T cell population (not gated on donor Class I) determined by CD4 and CD8 staining. Cells were stained with CD8-PE and CD4-TC. Percentages of less than 0.5% were considered not detectable (NDT).

Immature DP T-cells are low in Class I expression, and acquire a higher Class I expression at final stages of maturation. Histograms of the whole cell populations in grafts containing DP as well as SP T-cells show a bimodal donor Class I distribution. These populations include a high expressing donor class I population and a population that is low in Class I, but also contains cells which stain below isotype control levels. Histogram analysis of SP CD4+ and CD8+ cells for donor Class I expression demonstrates that mature T-cells in the BTS grafts express high levels of donor Class I. Immature DP T-cells however, express low to negative levels.

It may be that fetal thymus-derived donor HLA-negative T-cells reside in the Class I low population, generating a chimeric of donor (bone/spleen) and host (thymus) T-cell populations. The observation that rare to undetectable levels of donor HLA-negative cells are found in mature T-cells indicate that the proportion of the whole T-cell population derived from the host thymus is low.

Spleen/Bone Grafts Contain CD4+ Cells in the Absence of a Thymic Microenvironment. We analyzed a series of SCID-hu grafts in which spleen and bone fragments were placed subcutaneously, and an HLA mismatched thymic fragment was placed under the kidney capsule. While donor (spleen/bone) derived T-cell repopulation was never seen in 11 thymic grafts analyzed, 10 of the spleen/bone grafts contained detectable levels of cells positive for both donor HLA and CD4, shown in Table 3. High levels of donor derived B-cells, as well as myeloid cells cells are observed. While cells positive for CD8 are not detectable above isotype controls, CD4 positive cells are easily seen. Data for 11 grafts are summarized in Table 3. All grafts maintained both B-cell and myeloid cells for at least 32 weeks post transplant In addition 10 of those grafts had levels of CD4+ cells ranging from 1.0 to 5.3%. In no case were CD8+ cells observed.

The thymus implants are analyzed using light and electron microscopic analysis of tissue slices; a dramatic increase in apoptotic figures is observed in comparison to infrequent apoptotic figures in uninfected controls. As judged by flow cytometry >4 weeks post-inoculation, there is a substantial inversion of the CD4/CD8 ratio and a substantial reduction in the absolute number and relative proportion of CD4+ CD8+ thymocytes. This inversion continues to increase. The presence of virus based on the amount of p24 per $10^6$ cells show a continuous increase during the period of observation.

In addition, the number of cells with the normal (2N) complement of DNA is determined for a control and HIV isolate 2 and 4 weeks post-infection. As compared to

TABLE 3

Distribution of human hemopoietic cell types in SB mouse grafts

| graft number | weeks post engraftment | engrafted tissue set | % CD4+ cells with donor HLA | % CD8+ cells with donor HLA | % CD19+ cells with donor HLA | % CD33+ cells with donor HLA |
|---|---|---|---|---|---|---|
| SB-1 | 32 | I/J | 1.1 | NDT | 42.8 | 2.3 |
| SB-2 | 32 | I/J | 1.3 | NDT | 8.4 | 1.3 |
| SB-3 | 32 | I/J | 5.3 | NDT | 20.6 | 1.5 |
| SB-4 | 32 | I/J | NDT | NDT | 22.9 | NDT |
| SB-5 | 32 | I/J | 1.6 | NDT | 40.6 | 4.0 |
| SB-6 | 32 | I/J | 5.0 | NDT | 50.1 | 3.3 |
| SB-7 | 32 | K/L | 2.8 | NDT | 47.1 | 4.0 |
| SB-8 | 32 | K/L | 2.5 | NDT | 42.6 | 3.0 |
| SB-9 | 32 | K/L | 2.1 | NDT | 45.1 | 1.6 |
| SB-10 | 32 | K/L | 3.0 | NDT | 48.5 | 2.9 |
| SB-11 | 32 | K/L | 2.0 | NDT | 47.0 | 1.9 |

SCID mice implanted with fetal spleen-bone (I,K) subcutaneously (donor) and HLA mismatched thymus (J,L) under the kidney capsule were sacrificed 32 weeks post transplant (weeks post). Spleen-bone grafts and thymus grafts were removed and separate single cell suspensions made. Thymus demonstrated no contribution from spleen-bone (donor) graft derived cells. Cells were stained with BB7.1-FITC (tissue I) or BB7.2-FITC (tissue K) plus either CD8-PE and CD4-TC or CD33-PE and CD19-TC. The percentage of cells positive for donor HLA was determined by analysis on a FACscan. Percentages of less than 0.5% were considered not detectable (NDT).

EXAMPLE 2

Infection of BTS Implants with Human Tropic Viruses

A. Infection of BTS implants with primary isolates of HIV. Primary isolates and molecularly-cloned isolates of HIV 1 are used to infect the human T cells in the BTS chimeras. Chimeric BTS mice are made as described in Example 1. A flank incision is made to expose the growing human BTS implant of anesthetized mice. A dose of $10^3$–$10^4$ infectious units (based on T.C.I.D.$^{50}$ on PHA blasts) is introduced by direct intrathymic inoculation. The mice are then maintained within microisolator cages inside a glove box. At varying time points, various determinations are made.

In general, after test animals are sacrificed, thymus implants are surgically removed. In some instances, portions of tissue are set aside for histological examination. Whole or partial implants are crushed between frosted microscope slides to yield a suspension of thymocytes. ~$10^6$ thymocytes in 50 μl PBS/2% FCS are stained with anti-CD 4-FITC and anti-CD8-PE conjugated monoclonal antibodies for flow cytometry analysis. ~$10^6$ thymocytes are suspended in a solution of 0.1% Triton/1% citrate/50 μg per ml propidium iodide in water for 1 hour, washed, and resuspended in PBS/2% FCS for flow cytometry analysis. Propidium iodide intercalates DNA and can be used to assess DNA content within a single cell.

controls, several weeks post-infection, a normal thymus has a small fraction of cells containing less than (<2 N) the normal complement of DNA, while an infected thymus has a order of magnitude more cells containing less than (<2 N) the normal complement of DNA.

Treatment with Cyclosporine A of HIV-infected implants. Following the above procedure, BTS mice are infected with an HIV isolate. Cyclosporine A is administered subcutaneously via an osmotic minipump over a period of several weeks. The rate of administration is ~24 mg/kg/day and is commenced at different periods post-inoculation. Administration is begun one week post-inoculation and continued until termination of experimental animals. Despite high levels of p24 being present in the cells in the thymus, the depletion of CD4 expressing thymocytes is substantially diminished as compared to untreated HIV-infected control mice.

Treatment with ddI and AZT of HJV-infected implants. BTS implanted mice as described in Example 1, which have received the implant greater than 20 weeks before treatment prior to infection are used in these experiments. The BTS implants are inoculated with primary patient isolates of HIV or with a molecular HIV clone (JR-CSF). In all cases, thymus p24 levels increases in a time-dependent manner, indicating productive infection of some thymic elements.

Concomitant to the increase in p24, thymus cellularity is greatly reduced, reflecting the ablation of thymocytes of the CD4+8− and CD4+8+ phenotypes. Expression of viral antigens can be localized in several cell types, including thymocytes and thymic stromal elements. In the absence of any therapy, HIV infection of the thymus leads to the elimination of a majority of developing thymocytes.

Starting one week after infection, ddI is provided at 100 μl daily i.p. injections at 12.5 mg/mi, while AZT is provided at 1 mg/ml in drinking water ad libitum. After several weeks, the animals are analyzed.

The CD4/CD8 ratio is determined for: controls where no drug is administered, and for the ddI and AZT regimens. The sample for FACS determination is prepared by crushing thymic implants between frosted slides to release thymocytes. Thymocytes are washed and counted, then $10^6$ cells in about 50 μl PBS, 2% FCS are stained with anti-CD4-FITC and anti-CD8-PE-conjugated antibodies. Where no virus is administered the CD4/CD8 ratio is greater than 1:1. When ddI is administered, the animals show normal cellularity and subset distribution. Animals receiving AZT have an intermediate response which is better then no drugs, but not as marked an improvement as those which receive ddI.

B. Infection of a BTS Implant with Cytomegalovirus. Primary isolates of human CMV are used to infect the human cells in the BTS chimeras. Chimeric BTS mice are made as described in Example 1. At least 1 month after implantation, the implants are exposed with an incision, and are inoculated under the surface of the exposed implant with a 30-guage needle with clinical isolates of human CMV. The virus is able to grow in the implant. At 7 and 15 days post inoculation, animals are sacrificed and the tissue removed, minced, sonicated and titered for the presence of human CMV by plaque assay on human fibroblasts. In general, viral titer peaks are observed after one week.

In a further study, the BTS implant is employed for the CMV infection, but ganciclovir is provided at varying concentrations in the drinking water. The mice are maintained on the drug for two weeks, beginning shortly after infection and the level of CMV infection determined at the end of the 2-week period. Following this procedure, the virus titer decreases with increasing concentrations of ganciclovir. At 1.5 mg/ml ganciclovir in drinking water administered ad libitum, the titer of virus at two weeks is significantly less than in the control animals receiving no drug.

In the next study, the mice are maintained for two weeks on the drug, then two weeks off the drug, and the level of viremia determined at the end of the 4-week period. While the virus titer in ganciclovir treated animals is lower than those which had not been given the drug, it is increased from the two week titer.

C. Infection of a BTS implant with Varicella Zoster Virus (VZV) Chimeric BTS mice are made as described in Example 1. The implant is infected with varicella-zoster virus (VZV). The BTS implant supports the growth of VZV and show areas of tissue destruction that co-localize with viral antigen. MRC-5 fetal lung fibroblasts infected with VZV are used as the inoculum. Approximately $1.5 \times 10^3$ VZV-infected cells are injected into the implants, then the implants are surgically removed 1 and 2 weeks post-infection. Virus titer is seen at both time points. At both times, 3 micron sections of the implants which had been formalin-fixed and paraffin embedded, then hematoxylin and eosin stained, shows damaged areas characterized by fibrosis, nuclear debris, and necrosis. These areas corresponded to the presence of VZV antigen as detected by immunohistochemical staining using a polyclonal human VZV-immune serum as the pimary antibody. Virus is also detected in the cortical region of the implants that did not yet appear to have cytopathic effects, indicating that VZV is spreading and replicating throughout the implant.

D. Infection of BTS Implant with Measles Virus. Two wild-type strains of measles virus are injected into a BTS implant made as described in Example 1. 1 and 2 weeks after inoculation, viral replication is measured by endpoint dilution assay on B95-8 cells for syncytia formation or by plaque formation of Vero cells. Cytopathic effect on thymocytes induced by measles infection is evaluated by FACS analysis with anti-CD4, CD8 and CD3 antibodies. The measles virus replicates and shows a cytopathic effect in the BTS implant.

EXAMPLE 3

Treatment of BTS Mice with Liposome Encapsulated Dichloromethylene Diphosphonate ($CL_2MDP$) to Reduce Host Macrophage Levels Elimination of endogenous mouse macrophages by treatment with $Cl_2MDP$ affects the number of circulating human blood cells derived from a BTS implant. Although a substantial number of human cells are present in the grafts, the number of human cells in the circulation remains low. Mice having a BTS implant for greater than 20 weeks, as described in Example 1, are tested for peripheral blood human cell content. The mice are then injected in the tail vein with 200 μl of either PBS, or liposome encapsulated $CL_2MDP$.

The liposome encapsulated $CL_2MDP$ is prepared with phosphatidyl choline and cholesterol according to the method described by Delemarre, et al. (1990) *Immunobiol.* 180:395–404; and Rooijen (1989) *J. Immunol Methods* 124:1–6. Briefly, 75 mg of phosphatidyl choline and 11 mg cholesterol are dissolved in chloroform in a round bottomed flask. After low vacuum rotary evaporation at 37° C. the lipids are dispersed by gentle rotation in 10 ml PBS in which 1.89 g dichloromethylene diphosphonate is dissolved. The resulting liposomes are washed twice at 100,000×g for 30 min. to remove free, non-encapsulated $CL_2MDP$. The liposomes are then suspended in 4 ml of phosphate buffered saline (PBS) to yield a "100%" stock.

A majority of mice, after injection, show a rise in human cells in the periphery several days post injection, which is maintained at least two weeks post injection, and returns to base level by ~3–4 weeks post-injection.

It is evident from the above results that early hematopoietic progenitors within the human fetal bone and spleen can produce B-cells and myeloid cells, as well as mature and intermediate stage T-cells when transplanted together with fetal thymic tissue in an immunocompromised host animal. A high proportion of grafts of fetal bone, thymus and spleen (BTS) transplanted at the same site subcutaneously had cells positive for CD4 and/or CD8, cells positive for CD19 as well as a population of cells expressing CD33 when analyzed for human hematopoietic lineages 7–9 months post transplant. Analysis with anti-human HLA Class I markers identified the cells as being derived from progenitors in the bone/spleen, indicating a common stem cell pool can give rise to long-term multipotential human hematopoiesis in an in vivo model.

This subject chimeric system provides a small animal model for human antibody production, and the analysis of human hematopoiesis, and its disease states. After engraftment, the implanted human tissue can be manipulated in a systematic way. The consequences of such manipulations can be read out by various methods, as described.

Hematopoietic cells derived from diseased marrow, e.g., as in leukemias or genetic disorders, may be introduced into previously implanted allogeneic fetal bone grafts to study malignancy and the effects of growth factors and/or drugs which might modulate normal hematopoiesis or disease states. For human gene therapy trials, this model can also serve as a valuable system to test the long-term expression of exogenous genes introduced into human hematopoietic cells. The model is also a valuable system for observing the effects of human tropic viral infection and therapy in an in vivo system.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A mouse host lacking functional syngeneic B-cells and T-cells due to a genetic defect that results in an inability to undergo germline DNA rearrangement at the loci encoding immunoglobulins and T-cell antigen receptors, comprising:
    a hybrid tissue providing long-term production, for greater than twenty weeks, of human myeloid cells, B-cells and lymphoid progenitor cells formed by viable normal human fetal bone fragments and normal human fetal spleen grown in juxtaposition.

2. A host according to claim 1, wherein said mouse has a homozygous mutation at the scid locus.

3. A host according to claim 1, wherein said mouse lacks expression of at least one of functional RAG-1 or RAG-2.

4. A method for producing a chimeric mouse capable of long term production, for areater than twenty weeks, of human myeloid cells, B-cells and lymphoid progenitor cells, said method comprising:
    implanting viable normal human fetal spleen and normal human fetal bone fragments in juxtaposition at a sub-cutaneous site in an immunocompromised mouse host lacking functional syngeneic B- and T-cells due to a genetic defect that results in an inability to undergo germline DNA rearrangement at the loci encoding immunoglobulins and T-cell antigen receptors;
    whereby said tissue forms a hybrid tissue providing long-term production, for greater than twenty weeks of human myeloid cells, B-lineage cells and lymphoid progenitor cells.

5. A method according to claim 4, wherein said mouse has a homozygous mutation at the scid locus.

6. A method according to claim 4, wherein said mouse lacks expression of at least one of functional RAG-1 or RAG-2.

7. A mouse host lacking functional syngeneic B-cells and T-cells due to a genetic defect that results in an inability to undergo germline DNA rearrangement at the loci encoding immunoglobulins and T-cell antigen receptors, comprising:
    a hybrid tissue providing long-term production, for at least twenty weeks, of human-myeloid cells, B-cells and T-cells formed by viable normal human fetal bone fragments, normal human fetal spleen tissue and normal human fetal thymus tissue grown in juxtaposition.

8. A host according to claim 7, wherein said mouse has a homozygous mutation at the scid locus.

9. A host according to claim 7, wherein said mouse lacks expression of at least one of functional RAG-1 or RAG-2.

10. A host according to claim 7, wherein said hybrid tissue is infected with a human tropic virus.

11. A method for producing a chimeric mouse capable of long term production, for at least twenty weeks, of human myeloid cells, B-cells and T-cells, said method comprising:
    implanting viable normal human fetal spleen, normal human fetal bone fragments and normal human fetal thymus tissue in juxtaposition at a sub-cutaneous site in an immunocompromised mouse host lacking functional syngeneic B- and T-cells due to a genetic defect that results in an inability to undergo germline DNA rearrangement at the loci encoding immunoglobulins and T-cell antigen receptors; and
    maintaining said host, whereby said tissue forms a hybrid tissue providing long-term production, for at least twenty weeks, of human myeloid cells, B-cells and T-cells.

12. A method according to claim 11, wherein said mouse has a homozygous mutation at the scid locus.

13. A method according to claim 11, wherein said mouse lacks expression of at least one of functional RAG-1 or RAG-2.

14. A method for determining the repertoire of lineages that are able to develop from a particular human hematopoietic progenitor cell type, said method comprising:
    implanting viable human fetal spleen, normal human fetal bone fragments and normal human fetal thymus tissue in juxtaposition at a subcutaneous site in an immunocompromised mouse host lacking functional syngeneic B- and T-cells due to a genetic defect that results in an inability to undergo germline DNA rearrangement at the loci encoding immunoglobulins and T-cell antigen receptors
    irradiating said hybrid tissue;
    injecting HLA mismatched human hematopoietic progenitor cells into the cavity of said human bone;
    maintaining said host, whereby said tissue forms a hybrid tissue allowing long-term production, of at least twenty weeks, of human myeloid cells, B-cells and T-cells; and
    determining the repertoire of lineages of hematopoietic cells that develop having the HLA type of said progenitor cells.

* * * * *